(12) United States Patent
Park et al.

(10) Patent No.: US 11,286,334 B2
(45) Date of Patent: Mar. 29, 2022

(54) METHOD OF PREPARING A LATENT HARDENER WITH IMPROVED STORAGE STABILITY THROUGH A DRY SURFACE TREATMENT

(71) Applicant: KOREA INSTITUTE OF SCIENCE AND TECHNOLOGY, Seoul (KR)

(72) Inventors: Jong Hyuk Park, Seoul (KR); Min Park, Seoul (KR); Tae Ann Kim, Seoul (KR); Jongwon Kim, Seoul (KR); Sung Min Jee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 10 days.

(21) Appl. No.: 16/788,519

(22) Filed: Feb. 12, 2020

(65) Prior Publication Data

US 2021/0155749 A1 May 27, 2021

(30) Foreign Application Priority Data

Nov. 26, 2019 (KR) .......................... 10-2019-0153481

(51) Int. Cl.
| | | |
|---|---|---|
| C07B 61/00 | (2006.01) | |
| C07C 277/00 | (2006.01) | |
| C07D 247/02 | (2006.01) | |
| C08G 59/24 | (2006.01) | |
| C08G 59/50 | (2006.01) | |
| C09J 163/00 | (2006.01) | |

(52) U.S. Cl.
CPC .......... *C08G 59/5006* (2013.01); *C07B 61/00* (2013.01); *C07C 277/00* (2013.01); *C07D 247/02* (2013.01); *C08G 59/245* (2013.01); *C08G 59/50* (2013.01); *C09J 163/00* (2013.01)

(58) Field of Classification Search
CPC ..... C07B 61/00; C07C 277/00; C07D 247/02; C08G 59/245; C08G 59/50; C09J 163/00
USPC ......................................................... 366/101
See application file for complete search history.

(56) References Cited

U.S. PATENT DOCUMENTS

2009/0152504 A1   6/2009   Komuro et al.

FOREIGN PATENT DOCUMENTS

| EP | 0304503 B1 | 6/1994 |
|---|---|---|
| EP | 1852452 A1 | 11/2007 |
| KR | 1020080039166 A | 5/2008 |
| KR | 1020090033182 A | 4/2009 |
| KR | 1020100082150 A | 7/2010 |
| KR | 1020100132863 A | 12/2010 |

(Continued)

OTHER PUBLICATIONS

Kim et al., KR 1020100132863 A machine translation in English, Dec. 20, 2010 (Year: 2010).*

*Primary Examiner* — David T Karst
(74) *Attorney, Agent, or Firm* — Rabin & Berdo, P.C.

(57) ABSTRACT

A method for preparing a latent hardener includes, in the order recited, introducing a hardener into a dry mixer that is a high-energy-type mixer; injecting carbon dioxide gas or an inert gas into the dry mixer; and mechanochemically deactivating only a surface of the hardener using the dry mixer. The hardener may be an amine-based adduct, an imidazole-based adduct, dicyandiamide, a dihydride-based compound, a dichlorophenyl dimethylurea compound and combinations thereof. The inert gas may be helium, nitrogen, argon, neon, krypton, and combinations thereof.

6 Claims, 7 Drawing Sheets

(56) References Cited

FOREIGN PATENT DOCUMENTS

| KR | 1020110121473 | A  | 11/2011 |
|----|---------------|----|---------|
| KR | 101809935     | B1 | 12/2017 |
| WO | 2013116907    | A1 | 8/2013  |

\* cited by examiner

METHOD OF PREPARING A LATENT HARDENER WITH IMPROVED STORAGE STABILITY THROUGH A DRY SURFACE TREATMENT

CROSS-REFERENCE TO RELATED APPLICATION

This application claims priority to and the benefit of Korean Patent Application No. 10-2019-0153481, filed on Nov. 26, 2019, the disclosure of which is incorporated herein by reference in its entirety.

BACKGROUND OF THE INVENTION

Field of the Invention

The present specification relates to a latent hardener with improved storage stability by deactivating only the surface of the hardener through a dry process, a one-component epoxy adhesive including the same, and a preparation method thereof. More specifically, the present specification relates to a latent hardener in which only the surface of the hardener is selectively deactivated under a carbon dioxide or inert gas atmosphere, a one-component epoxy adhesive including the same, and a preparation method thereof.

DESCRIPTION ABOUT NATIONAL SUPPORT RESEARCH AND DEVELOPMENT

This study is made by the support of the Ministry of Trade, Industry and Energy of the Republic of Korea under the supervision of LG Chem., the project name thereof is Development of material and part technology (R&D), and the subject name thereof is the nano-composite material for ultra-lightweight structures (Subject Identification No.: 1415158382).

Description of the Related Art

An epoxy adhesive is composed of a hardener that initiates or accelerates a curing reaction with an epoxy resin in the form of a polymer.

In the case of a two-component epoxy adhesive in the related art, a resin and a hardener are stored in a separated state, and the two materials are mixed immediately before use and used as an adhesive. These processes lack the convenience of operation and may cause problems such as possible measurement errors. Accordingly, a one-component epoxy adhesive in which an epoxy resin and a hardener are mixed in advance is preferred.

However, the one-component epoxy adhesive has a disadvantage in that it is difficult to store the one-component epoxy adhesive for a long period of time because the mixed epoxy resin and hardener may gradually react at room temperature. In order to compensate for this disadvantage, it is essential to develop a latent hardener in which a curing reaction does not occur at room temperature and occurs only when an external stimulus such as light, moisture, or heat is applied.

As a method for preparing a latent hardener, a method for encapsulating the surface of the hardener is commonly used. A protective layer may be formed on the surface of the hardener by a method of dissolving an organic material usually capable of reacting with a hardener in an organic solvent, dispersing the hardener in the solution, and applying heat. In particular, in the case of an amine-based adduct hardener, a method of forming a protective layer on the surface of the hardener using an epoxy precursor or isocyanate has been proposed (EP Patent Publication No. 0 304 503 B1 and EP Patent Publication No. 1 852 452 A1).

However, this method is a wet method that requires a large amount of organic solvent, and has disadvantages in that additional cost and time are consumed in the process of removing the organic solvent after the process and an environmental pollution problem may be caused. Therefore, there is a need for developing a method for forming a protective layer on the surface of a hardener without using an organic solvent.

SUMMARY OF THE INVENTION

An object of the present disclosure is to provide a latent hardener in which only the surface of the hardener is deactivated under an atmosphere of carbon dioxide or an inert gas such as nitrogen and argon, and a preparation method thereof.

Another object of the present disclosure is to provide a one-component adhesive with improved storage stability by mixing the latent hardener with an epoxy resin.

To achieve the objects, an exemplary embodiment of the present disclosure provides a method for preparing a latent hardener, the method including: introducing a hardener into a dry high energy-type mixer; injecting carbon dioxide gas or an inert gas into the dry high energy-type mixer; and mechanochemically deactivating only a surface of the hardener using the dry high energy-type mixer.

An exemplary embodiment of the present disclosure provides a method for preparing a latent hardener, the method including: introducing a hardener into a vessel or mixer capable of adjusting the composition of a gas atmosphere; injecting carbon dioxide gas into the vessel or mixer; and deactivating only a surface of the hardener using the vessel or mixer to react the surface of the hardener with carbon dioxide.

An exemplary embodiment of the present disclosure provides a latent hardener having a core-shell structure, including: a hardener which is a core; and a protective layer which is a shell on the core hardener.

An exemplary embodiment of the present disclosure provides a latent hardener having a core-shell structure, including: a hardener which is a core; and a protective layer which is a shell on the core hardener, in which the protective layer is formed by allowing the hardener to react with carbon dioxide.

An exemplary embodiment of the present disclosure provides a one-component epoxy adhesive including: an epoxy resin; and the above-described latent hardener.

REFERENCE NUMERALS OF THE DRAWINGS

Figure 1:
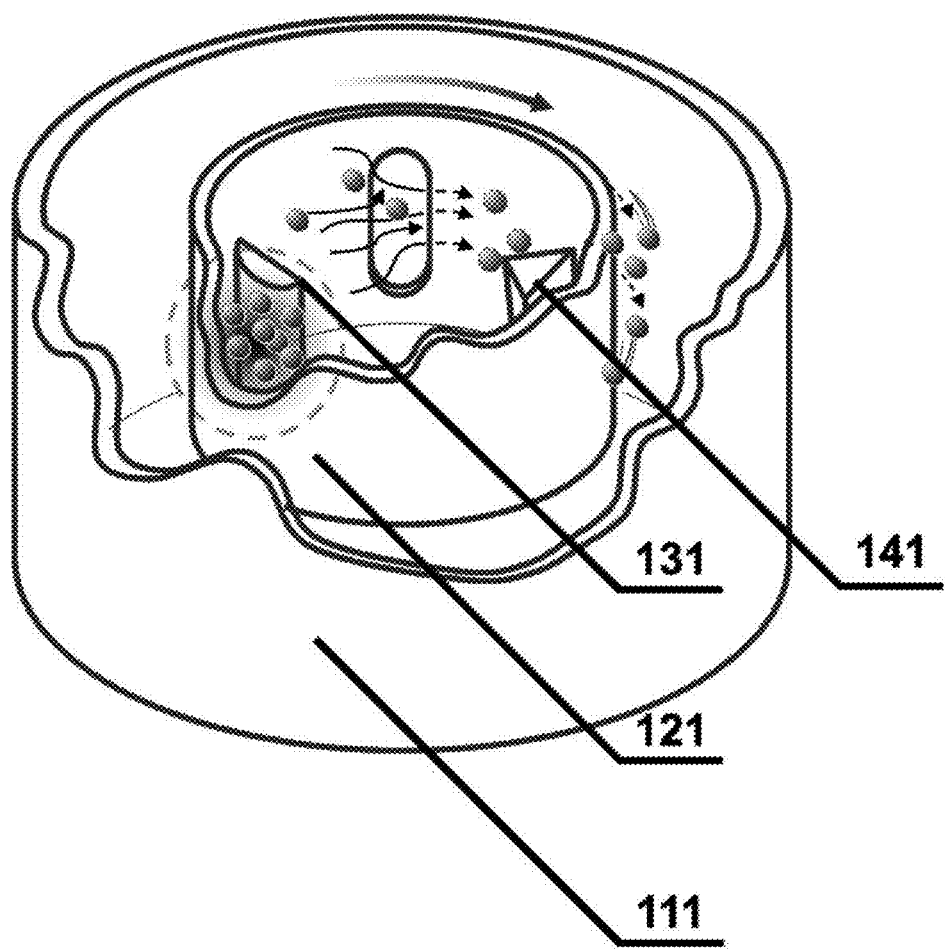
FIG. 1 is a schematic view of a reactor for inducing a mechano-chemical reaction according to an embodiment of the present disclosure.

111: a vessel capable of adjusting temperature
121: a rotating inner vessel
131: a pressure-applying arm
141: a scraper
211: a vessel capable of adjusting temperature
212: a rotating blade

DETAILED DESCRIPTION OF THE PREFERRED EMBODIMENTS

Hereinafter, preferred examples of the present disclosure will be described in detail with reference to the accompanying drawings.

The examples of the present disclosure disclosed herein are exemplified for the purpose of describing the examples of the present disclosure only, and the examples of the present disclosure may be carried out in various forms and should not be construed to be limited to the examples described herein.

Since the present disclosure may have various changes and different forms, it should be understood that the Examples are not intended to limit the present disclosure to specific disclosure forms and they include all the changes, equivalents and replacements included in the spirit and technical scope of the present disclosure.

When one part "includes" one constituent element in the present specification, unless otherwise specifically described, this does not mean that another constituent element is excluded, but means that another constituent element may be further included.

In the present specification, the "latent hardener" means a hardener which does not act as a hardener unless the hardener is under a specific curing condition.

In the present specification, the "dry high energy-type mixer" refers to a device capable of applying a mechanical force such as strong shearing force and compression force to particles and allows selective implementation of a chemical reaction on the surface of particles by heat energy generated thereby.

Representatively, it means a Mechanofusion. The reactivity of the surface layer of the hardener that is subjected to the treatment process as described above remarkably deteriorates, but the reactivity inside the hardener is maintained, so that it is possible to improve the storage stability in the epoxy resin without significantly changing the curing characteristics.

Method for Preparing Latent Hardener

Hereinafter, a method for preparing a latent hardener according to an embodiment of the present disclosure will be described.

Exemplary embodiments of the present disclosure provide a method for preparing a latent hardener, the method including: introducing a hardener into a dry high energy-type mixer; injecting carbon dioxide gas or an inert gas into the dry high energy-type mixer; and mechanochemically deactivating only a surface of the hardener using the dry high energy-type mixer.

For a capsule-type latent hardener in the related art, a method for preparing the latent hardener using a large amount of an organic solvent is generally used. This method may form a protective film on the surface of the hardener, but has problems in that the method is not eco-friendly and the storage stability deteriorates.

In order to overcome these problems, a technique using different types of powdery particles has been proposed, but the technique has difficulties in securing a uniform protective film on the surface of the hardener, and the curing behavior of the hardener may significantly vary due to residual particles that are not attached to the surface of the hardener.

The method for preparing a latent hardener according to an embodiment of the present disclosure provides a latent hardener, which is characterized in that the surface of the hardener is selectively deactivated by Mechanofusion treatment in a state of injecting carbon dioxide gas or an inert gas, and the Mechanofusion is characterized by being performed by rotating a chamber itself of a dry high energy-type mixer or a rotor inside the chamber in order to apply a mechanical force (shearing force, compression force, and friction force) to samples.

In contrast, the method for preparing a latent hardener according to an embodiment of the present disclosure is a method for utilizing carbon dioxide gas or an inert gas for a reaction, and carbon dioxide or the inert gas may be uniformly distributed and reacted on the surface of a reactant material, and thus may secure high reproducibility and homogeneity. Also, since an excessive amount of the carbon dioxide gas or the inert gas is naturally discharged after the process, unreacted materials other than the hardener do not remain, so that it is possible to prevent other side effects caused by residues. Further, the preparation method is a dry process, and may reduce the cost and time and is eco-friendly because the process of supplying or treating a solvent is omitted.

In exemplary embodiments, the inert gas may be one or more selected from the group consisting of helium, nitrogen, argon, neon, and krypton.

In exemplary embodiments, the carbon dioxide or inert gas may be injected into a dry high energy-type mixer at a flow rate of 0.1 to 10 L/min, and for example, the flow rate may be 0.3 L/min or more, 0.5 L/min or more, or 0.7 L/min or more, and may be 7 L/min or less, 5 L/min or less, 3 L/min or less, or 2 L/min or less, but the flow rate is associated with the amount of the material depending on the size of the reactor or the reaction rate, and is not limited thereto.

In exemplary embodiments, the deactivating of only the surface of the hardener may be performed for 1 to 240 minutes, for example, 5 minutes or more, 10 minutes or more, 15 minutes or more, 20 minutes or more, or 25 minutes or more, and 200 minutes or less, 150 minutes or less, 100 minutes or less, 50 minutes or less, or 40 minutes or less.

When the reaction time is less than 1 minute, the reaction may not be performed, and as the reaction time is increased, the effect of the protective layer is more improved, but the reaction is stabilized after a predetermined time, for example, 240 minutes or more, and thus may not be further performed.

Further, the stabilization time changes depending on the temperature, and may vary depending on the control because the reaction is stabilized in a short time at a high temperature and the stabilization time is prolonged at a low temperature.

In exemplary embodiments, the dry high energy-type mixer may include a vessel 111 capable of adjusting temperature, a rotating inner vessel 121, a pressure-applying arm 131, and a scraper 141, and may be a Mechanofusion including a vessel 111 capable of adjusting temperature, a rotating inner vessel 121, a pressure-applying arm 131, and a scraper 141.

After a hardener is first introduced into a Mechanofusion, stress such as shearing force, compression force, and friction force may be imparted to the hardener by centrifugal force when the inner vessel 121 is rotated in a state in which the inside of the reactor is filled with carbon dioxide gas or an inert gas. As a result, frictional heat is generated on the surface of the hardener particles, and the carbon dioxide gas or the inert gas may selectively react only on the surface of the hardener. By such a reaction, the surface of the latent hardener may be modified into a state of low reactivity (inert state), so that the storage stability may be enhanced.

However, the case where the preparation process is performed by injecting an active gas makes it difficult to adjust the degree of reaction with the hardener, and may cause a negative effect on curing performance.

In exemplary embodiments, the method for preparing a latent hardener may be performed by adjusting one or more conditions selected from the group consisting of a rotation speed of the inner vessel 121, a gap between the inner vessel 121 and the pressure-applying arm 131, a type of gas, a gas inflow amount, and temperature. It is possible to control the shape and structure of the hardener according to the rotation speed, which may affect the storage stability, and the gap distance between the inner vessel 121 and the pressure-applying arm 131 may affect the shape and storage stability of the hardener by affecting the generation of pressure and thermal energy.

Specifically, at the time of preparing a latent hardener, the reaction rate is low at a low temperature such as room temperature (27° C.) so that the process efficiency is reduced, but there is an advantage in that the reaction is easily controlled as the reaction rate is slowed down. In order to increase the process efficiency, the reaction temperature may be increased, but when the process is performed at an excessively high temperature (60 to 120° C.), inactivation (curing) proceeds up to the core of the hardener so that a function as an epoxy hardener may be lost.

In exemplary embodiments, the rotation speed of the inner vessel 121 may be 20 to 15,000 rpm, the gap between the inner vessel 121 and the pressure-applying arm 131 may be 0.2 to 10 mm, and the temperature may be 20 to 120° C.

For example, the rotation speed may be 100 rpm or more, 500 rpm or more, 700 rpm or more, 900 rpm or more, and may be 10,000 rpm or less, 5,000 rpm or less, 3,000 rpm or less, or 2,000 rpm or less.

For example, the gap may be 0.4 mm or more, 0.6 mm or more, or 0.8 mm or more, and may be 8 mm or less, 6 mm or less, 4 mm or less, or 2 mm or less.

For example, the temperature may be 20 to 60° C., 20 to 40° C., or 25 to 30° C., and may be preferably 27° C. When the rotation speed is too slow, particles are aggregated or scattered so that the homogeneity of the surface reaction deteriorates, and when the rotation speed is excessively high, the mechanical energy is increased so that high heat may be applied to the hardener. Further, when the gap is narrowed or the temperature of the chamber is higher than 120° C., high heat is applied to the hardener so that an undesired curing reaction may proceed.

In exemplary embodiments, the hardener may be one or more selected from the group consisting of an amine-based adduct, an imidazole-based adduct, dicyandiamide, a dihydride-based compound, and a dichlorophenyl dimethylurea compound, and may be preferably an amine adduct-based PN-23 manufactured by Ajinomoto Fine-Techno Co., Inc.

Exemplary embodiments of the present disclosure provide a method for preparing a latent hardener, the method including: introducing a hardener into a vessel or mixer capable of adjusting the composition of a gas atmosphere; injecting carbon dioxide gas into the vessel or mixer; and reacting only a surface of the hardener with carbon dioxide using the vessel or mixer.

In exemplary embodiments, the carbon dioxide gas may be injected into the vessel or mixer at a flow rate of 0.1 to 10 L/min.

In exemplary embodiments, the reacting of only the surface of the hardener with the carbon dioxide may be performed for 1 to 240 minutes.

In exemplary embodiments, the vessel or mixer may include a vessel 211 capable of adjusting temperature and a rotating blade 212, and the method for preparing a latent hardener may be performed by adjusting one or more conditions selected from the group consisting of temperature of the vessel 211 capable of adjusting temperature, a rotation speed of the rotating blade 212, a type of gas, a gas inflow amount, and temperature.

In exemplary embodiments, the temperature of the vessel 211 capable of adjusting temperature may be 20 to 60° C., and the rotation speed of the rotating blade 212 may be 20 to 15,000 rpm.

Latent Hardener

Exemplary embodiments of the present disclosure provide a latent hardener having a core-shell structure, including: a hardener which is a core; and a protective layer which is a shell on the core hardener.

The latent hardener according to an embodiment of the present disclosure is characterized by including a protective layer in which only the surface of the hardener is selectively deactivated by Mechanofusion treatment into which carbon dioxide gas or an inert gas is injected.

Additionally, the latent hardener according to an embodiment of the present disclosure may secure high reproducibility and homogeneity because a carbon dioxide reaction may be uniformly distributed on the surface of a material by a method for utilizing carbon dioxide gas for a reaction, and since an excessive amount of carbon dioxide gas is naturally discharged after the process, unreacted materials other than the hardener do not remain, so that it is possible to prevent other side effects caused by residues. Further, the method is a dry process, and may reduce the cost and time and is eco-friendly because the process of supplying or treating a solvent is omitted.

In exemplary embodiments, the hardener may have a size of 0.1 to 100 μm, for example, 1 μm or more, 10 μm or more, 20 μm or more, 30 μm or more, or 40 μm or more, and a size of 90 μm or less, 80 μm or less, 70 μm or less, or 60 μm or less. When the size is less than 0.1 μm, the surface area is increased when the hardener particles are dispersed in an epoxy resin, so that the viscosity may be increased and the reactivity may be enhanced, whereas when the size is more than 100 μm, the surface area is decreased, so that the reactivity may be reduced and the viscosity may be increased.

In exemplary embodiments, the protective layer may be deactivated through a mechanochemical reaction under a carbon dioxide or inert gas atmosphere using a high energy-type mixer.

In exemplary embodiments, the protective layer may have a thickness of 0.1 to 100 nm, for example, 1 nm or more, 10 nm or more, 20 nm or more, or 30 nm or more, and a thickness of 90 nm or less, 80 nm or less, or 70 nm or less. When the thickness is less than 0.1 nm, the effect of the protective layer is so slight that the process is meaningless, and when the thickness is more than 100 nm, the protective effect is good, but the fast-reactivity (rapid curability) may be hindered.

In exemplary embodiments, the inert gas may be one or more selected from the group consisting of helium, nitrogen, argon, neon, and krypton.

Exemplary embodiments of the present disclosure provide a latent hardener having a core-shell structure, including: a hardener which is a core; and a protective layer which is a shell on the core hardener, in which the protective layer is formed by allowing the hardener to react with carbon dioxide.

In exemplary embodiments, the protective layer formed by allowing the hardener to react with the carbon dioxide may be one or more selected from the group consisting of an amine-based adduct, an imidazole-based adduct compound, a carbamate compound, and polycarbonate.

Exemplary embodiments of the present disclosure provide a one-component epoxy adhesive including: an epoxy resin; and the above-described latent hardener.

The one-component epoxy adhesive according to an embodiment of the present disclosure includes a latent hardener in which the surface of the hardener is selectively deactivated by treatment with carbon dioxide gas and an inert gas, has high resistance to external impact, and has a long pot life.

In addition, since only the surface of the hardener is selectively deactivated without any chemical modification inside the hardener, there is an advantage in that during a curing reaction with an epoxy resin, the heat of curing reaction is not decreased and only the storage stability is enhanced.

In exemplary embodiments, the latent hardeners may be dispersed in the epoxy resin.

In exemplary embodiments, the epoxy resin may be one or more selected from the group consisting of bisphenol-A type epoxy, bisphenol-F type epoxy, novolac epoxy, flame-retardant epoxy, cycloaliphatic epoxy, and rubber modified epoxy, and may be preferably bisphenol-A type epoxy, and particularly, bisphenol A diglycidyl ether (DGEBA).

The present disclosure will be described in more detail through the following examples. However, the examples are provided for exemplifying the present disclosure, and the scope of the present disclosure is not limited thereto.

PREPARATION EXAMPLES—PREPARATION OF SURFACE DEACTIVATED LATENT HARDENER

Preparation Example 1

A hardener (an amine adduct-based PN-23 manufactured by Ajinomoto Fine-Techno Co., Inc.) was put into a reactor (a Mechanofusion manufactured by Hosokawa Micron Corp.) as illustrated in FIG. 1, and the process time, the temperature of an outer vessel 111, and a rotation speed of an inner vessel were set at 30 minutes, 27° C., and 1,000 rpm, respectively. Further, a gap between a pressure-applying arm 131 and the inner vessel 121 was fixed at 1 mm, and carbon dioxide was allowed to flow at 1 L/min.

Preparation Example 2

A latent hardener was prepared in the same manner as in Preparation Example 1, except that nitrogen instead of carbon dioxide was allowed to flow at 1 L/min.

Preparation Example 3

A latent hardener was prepared in the same manner as in Preparation Example 1, except that argon instead of carbon dioxide was allowed to flow at 1 L/min.

Preparation Example 4

A latent hardener was prepared in the same manner as in Preparation Example 1, except that oxygen instead of carbon dioxide was allowed to flow at 1 L/min.

Preparation Example 5

A latent hardener was prepared in the same manner as in Preparation Example 1, except that the reactor as illustrated in FIG. 1 was not used, the aforementioned hardener was put into an oven, the process time and the temperature were set at 30 minutes and 60° C., respectively, and carbon dioxide was allowed to flow at 1 L/min.

Preparation Example 6

A latent hardener was prepared in the same manner as in Preparation Example 5, except that nitrogen instead of carbon dioxide was allowed to flow at 1 L/min.

Preparation Example 7

A latent hardener was prepared in the same manner as in Preparation Example 5, except that argon instead of carbon dioxide was allowed to flow at 1 L/min.

Preparation Example 8

A latent hardener was prepared in the same manner as in Preparation Example 5, except that oxygen instead of carbon dioxide was allowed to flow at 1 L/min.

Preparation Example 9

Figure 2:
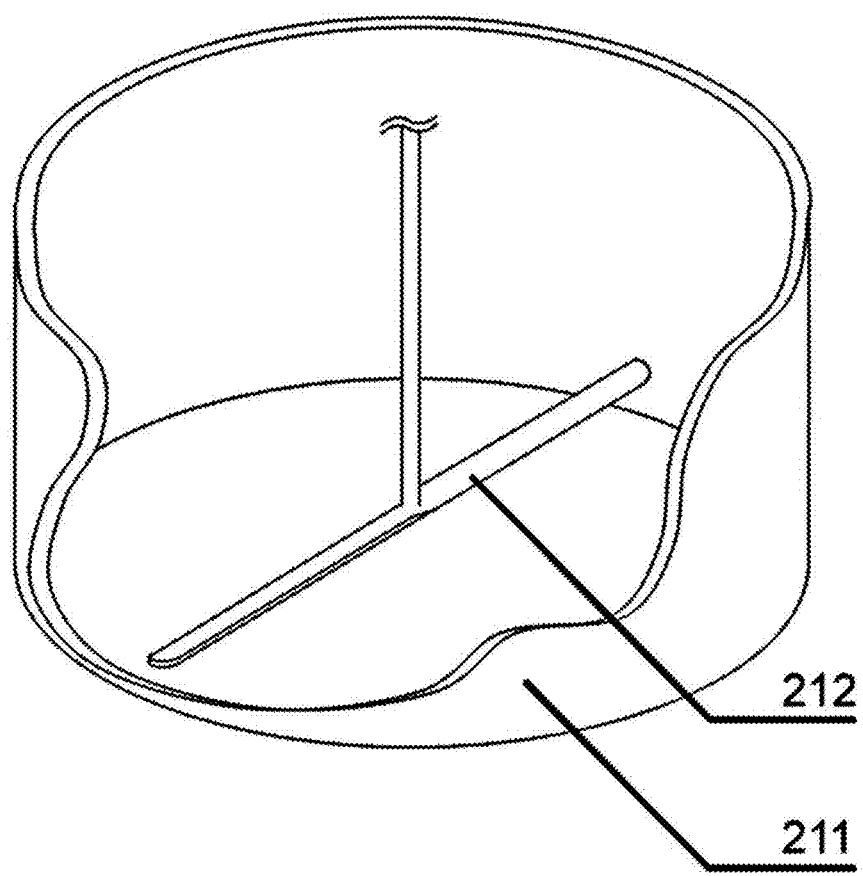
FIG. 2 is a schematic view of a reactor that induces a reaction by scattering (dispersing) hardener particles according to an embodiment of the present disclosure.

A latent hardener was prepared in the same manner as in Preparation Example 1, except that the aforementioned hardener was put into a reactor (Henschel Mixer) as illustrated in FIG. 2 instead of the reactor as illustrated in FIG. 1, and the process time, the temperature of an outer vessel 211, and a rotation speed of a scattering (dispersing) blade 212 were set at 30 minutes, 27° C., and 1,000 rpm, respectively.

Furthermore, carbon dioxide was allowed to flow at 1 L/min. Specifically, the Henschel Mixer is a reactor which uniformly mixes particles through the rotation of a blade (propeller), and no liquid was put into the reactor.

Preparation Example 10

A latent hardener was prepared in the same manner as in Preparation Example 9, except that nitrogen instead of carbon dioxide was allowed to flow at 1 L/min.

Preparation Example 11

A latent hardener was prepared in the same manner as in Preparation Example 9, except that argon instead of carbon dioxide was allowed to flow at 1 L/min.

Preparation Example 12

A latent hardener was prepared in the same manner as in Example 9, except that oxygen instead of carbon dioxide was allowed to flow at 1 L/min.

TABLE 1

| | Temperature (° C.) | Reactor | Inflow gas |
|---|---|---|---|
| Preparation Example 1 | 27 | Mechanofusion | Carbon dioxide |
| Preparation Example 2 | 27 | Mechanofusion | Nitrogen |
| Preparation Example 3 | 27 | Mechanofusion | Argon |
| Preparation Example 4 | 27 | Mechanofusion | Oxygen |
| Preparation Example 5 | 60 | Oven | Carbon dioxide |
| Preparation Example 6 | 60 | Oven | Nitrogen |
| Preparation Example 7 | 60 | Oven | Argon |
| Preparation Example 8 | 60 | Oven | Oxygen |
| Preparation Example 9 | 27 | Henschel Mixer | Carbon dioxide |
| Preparation Example 10 | 27 | Henschel Mixer | Nitrogen |
| Preparation Example 11 | 27 | Henschel Mixer | Argon |
| Preparation Example 12 | 27 | Henschel Mixer | Oxygen |

EXAMPLES—PREPARATION OF ONE-COMPONENT EPOXY ADHESIVE

Example 1

10 g of the surface deactivation-treated latent hardener in Preparation Example 1 was mixed with 100 g of an epoxy resin (bisphenol A diglycydiyl ether, DGEBA) by a co-rotating mixer to be 10 parts per hundred resin (phr). The mixing conditions were based on mixing at 2,000 rpm for 10 minutes and at 2,200 rpm for 5 minutes. Specifically, the co-rotating mixer is a non-contact type dispersing device which disperses a latent hardener in an epoxy resin, and may be used to finally produce an epoxy-hardener composite resin (one-component epoxy adhesive).

Example 2

A one-component epoxy composite resin was prepared in the same manner as in Example 1, except that 10 g of the latent hardener in Preparation Example 2 was used instead of the latent hardener in Preparation Example 1.

Example 3

A latent hardener was mixed with the epoxy in the same manner as in Example 1, except that 10 g of the latent hardener in Preparation Example 3 was used instead of the latent hardener in Preparation Example 1.

Example 4

A latent hardener was mixed with epoxy in the same manner as in Example 1, except that 10 g of the latent hardener in Preparation Example 4 was used instead of the latent hardener in Preparation Example 1.

Example 5

A latent hardener was mixed with the epoxy in the same manner as in Example 1, except that 10 g of the latent hardener in Preparation Example 5 was used instead of the latent hardener in Preparation Example 1.

Example 6

A latent hardener was mixed with the epoxy in the same manner as in Example 1, except that 10 g of the latent hardener in Preparation Example 6 was used instead of the latent hardener in Preparation Example 1.

Example 7

A latent hardener was mixed with the epoxy in Example 1, except that 10 g of the general hardener was used before the preparation instead of the latent hardener in Preparation Example 7.

Example 8

A latent hardener was mixed with the epoxy in the same manner as in Example 1, except that 10 g of the latent hardener in Preparation Example 8 was used instead of the latent hardener in Preparation Example 1.

Example 9

A latent hardener was mixed with the epoxy in the same manner as in Example 1, except that 10 g of the latent hardener in Preparation Example 9 was used instead of the latent hardener in Preparation Example 1.

Example 10

A one-component epoxy composite resin was prepared in the same manner as in Example 1, except that 10 g of the latent hardener in Preparation Example 10 was used instead of the latent hardener in Preparation Example 1.

Example 11

A one-component epoxy composite resin was prepared in the same manner as in Example 1, except that 10 g of the latent hardener in Preparation Example 11 was used instead of the latent hardener in Preparation Example 1.

Example 12

A one-component epoxy composite resin was prepared in the same manner as in Example 1, except that 10 g of the latent hardener in Preparation Example 12 was used instead of the latent hardener in Preparation Example 1.

Comparative Example 1

A one-component epoxy adhesive was prepared in the same manner as in Example 1, except that 10 g of a hardener which was not surface-treated (an amine adduct-based PN-23 manufactured by Ajinomoto Fine-Techno Co., Inc.) was used.

TEST EXAMPLES

Test Example 1—Observation of Surface Deactivation-Treated Hardener

According to an example of the present disclosure, the surface of a latent hardener (Preparation Example 1) in which the surface of a general hardener (an amine adduct-based PN-23 manufactured by Ajinomoto Fine-Techno Co., Inc.) is deactivated was observed by a scanning electron microscope (SEM) (FIG. 3).

Figure 3A:
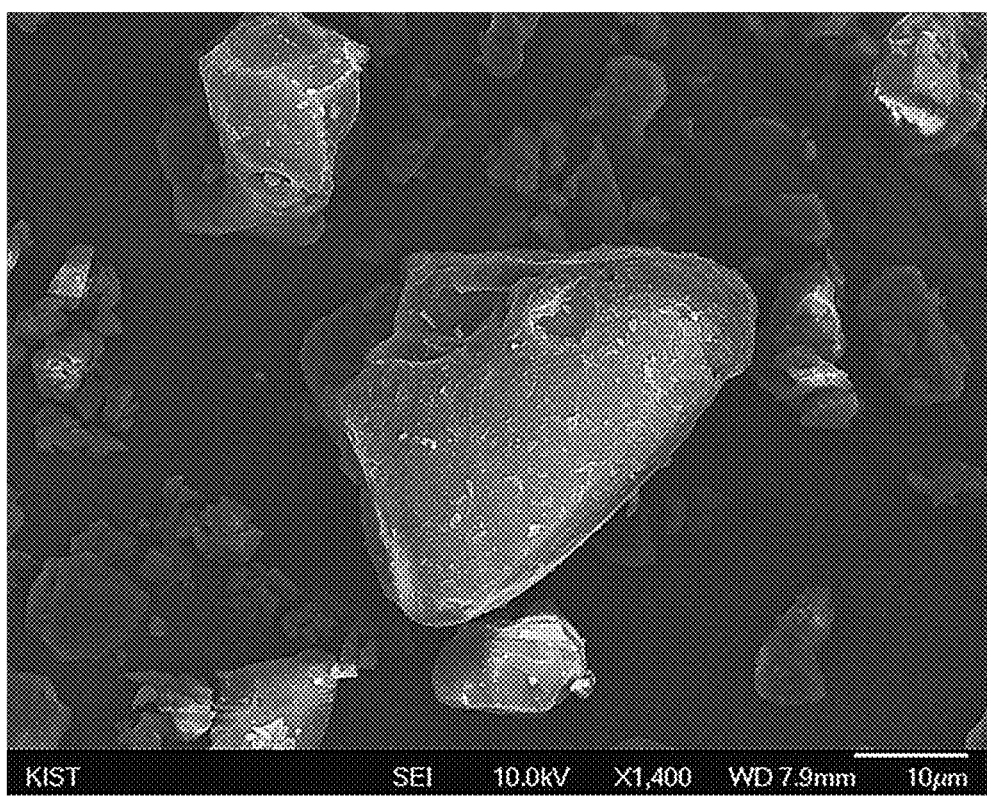
FIGS. 3A and 3B are SEM photographs of a latent hardener (before 3A/after 3B) in which surface reaction groups are deactivated according to Preparation Example 1, which is an example of the present disclosure.
Figure 3B:
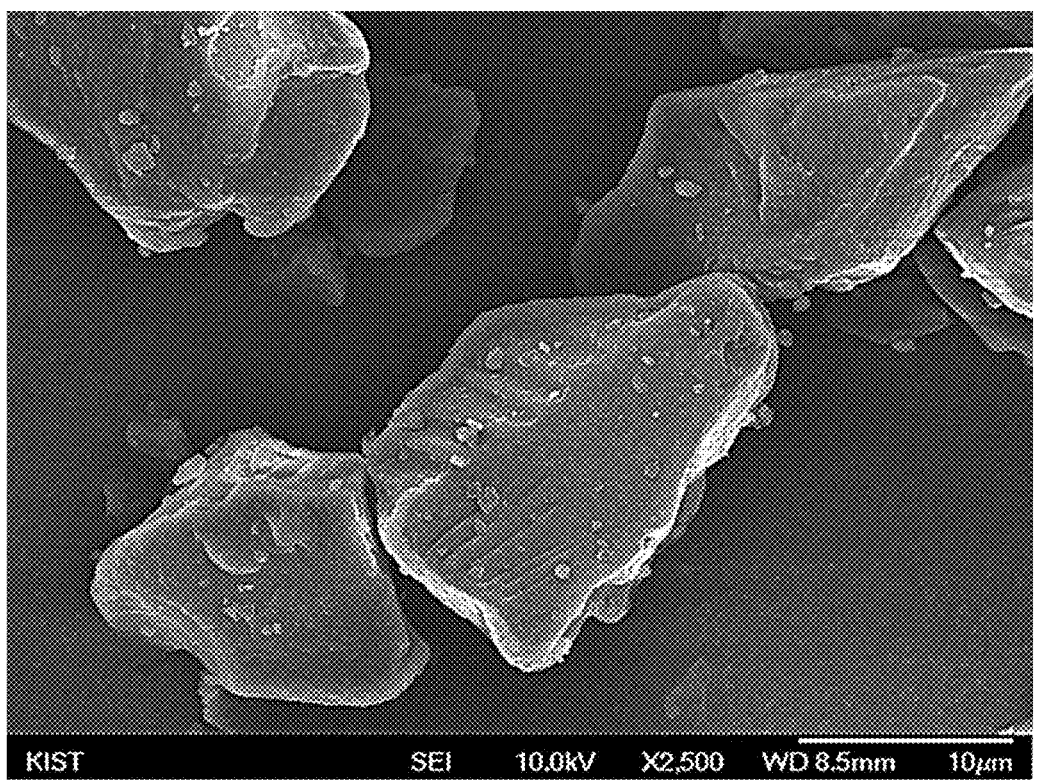

Referring to FIGS. 3A and 3B, it could be confirmed that the shape and surface of the hardener 3b after the treatment were not significantly changed as compared to those of the hardener 3a before the treatment. That is, the present process method may maintain the shape of the existing hardener, and thus may prevent the change in curing behavior according to the change in size and shape.

Test Example 2—Surface Analysis of Hardener

Figure 4:
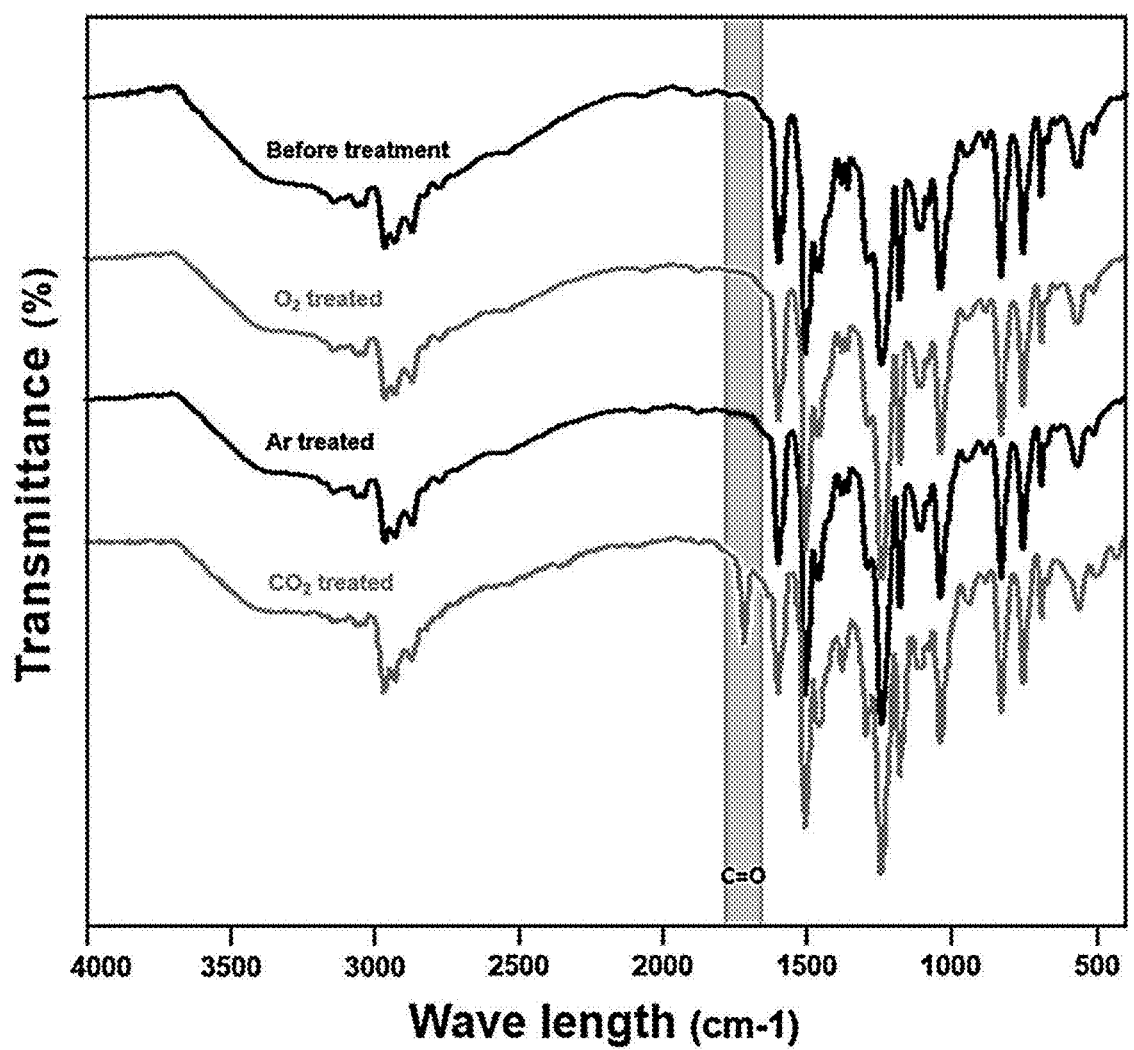
FIG. 4 is an FT-IR graph of a latent hardener in which the gas atmosphere is changed according to an example of the present disclosure.

FIG. 4 is a Fourier transform infrared spectroscopy (FT-IR) analysis graph of hardeners in Preparation Example 1, Comparative Example 1, and Preparation Examples 3 (argon) and 4 (oxygen). Through the graph, it can be confirmed that only when carbon dioxide was used as an injection gas, a carbonyl (C=O) functional group has been newly formed.

Test Example 3—Thermal Analysis

The changes in calorific values of the one-component epoxy resins according to Example 1 and Comparative Example 1 were measured by a differential scanning calorimeter (DSC). Specifically, the hardeners used for measurement were the latent hardener which has been surface deactivation-treated by the reactor as illustrated in FIG. 1 (Example 1) and the hardener before the treatment (Comparative Example 1).

The Mechanofusion (reactor as illustrated in FIG. 1) used for the preparation process may induce a chemical reaction by selectively applying stress to the surface. In order to confirm the effect of the present process method, the curing behaviors thereof were compared using an oven as a reactor as in Examples 5 to 8 or using a Henschel Mixer as in Examples 9 to 12 (Table 2 and FIG. 5).

Figure 5:
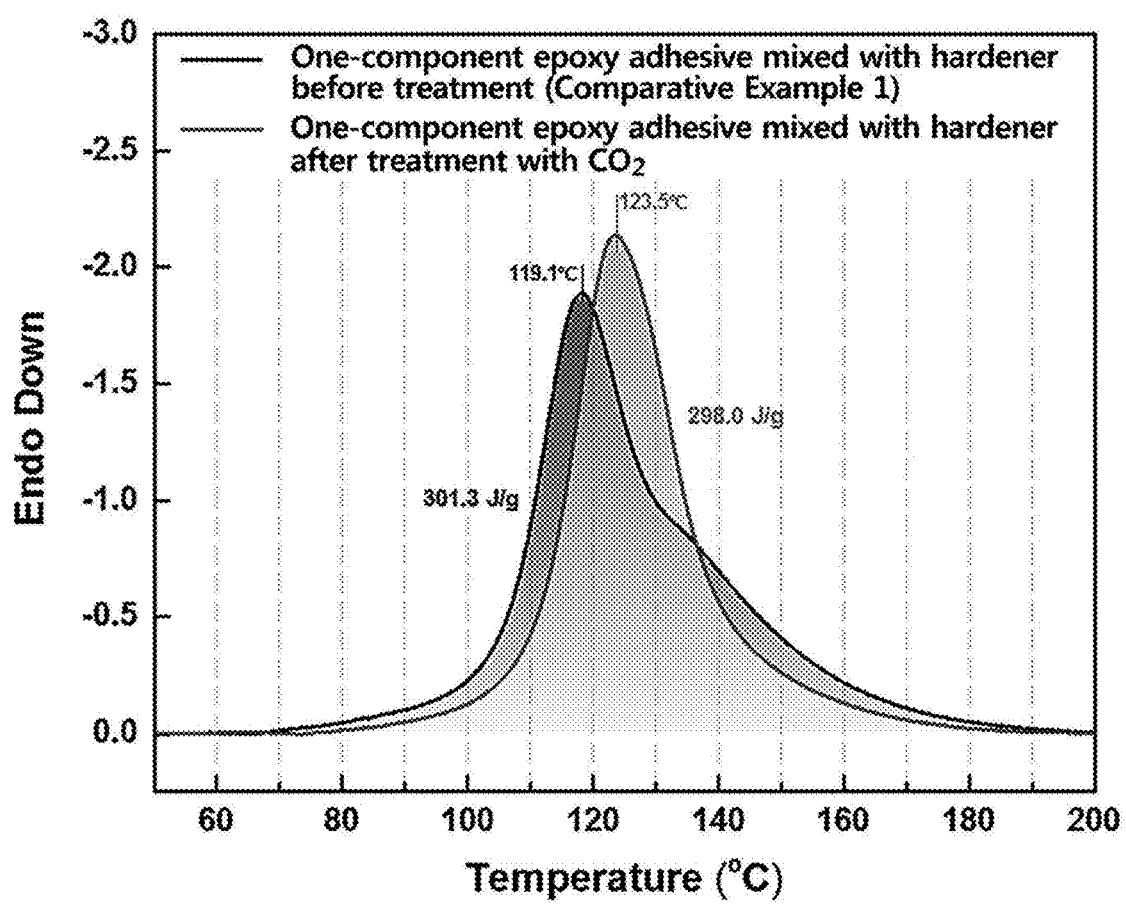
FIG. 5 is a graph illustrating DSC measurement results of a one-component epoxy adhesive prepared according to an example of the present disclosure.

FIG. 5 is a result of measuring the curing heat by mixing the latent hardener prepared by the method (Example 1) with an epoxy resin, and it was confirmed that there was no difference in curing heat when compared with the hardener before the surface treatment (Comparative Example 1).

Referring to the following Table 2, it can be confirmed that the curing heat of Example 1 (Mechanofusion, carbon dioxide) prepared by the surface deactivation method proposed by the present specification is not significantly changed as compared to Comparative Example 1 (untreated hardener). Further, it can be seen that when the preparation process is performed using an active gas as in Example 4 (Mechanofusion, oxygen), the curing heat is significantly decreased, and thus curing performance deteriorates.

The case where the process is performed in an oven (Examples 5 to 8) shows the tendency for the curing heat to be decreased on the whole because it is difficult for the selective deactivation reaction to be performed. When the Henschel Mixer is used (Examples 9 to 12), stress is not sufficiently transferred to the surface, and thus the deactivation reaction does not proceed properly, and accordingly, it can be confirmed that the range of change in curing heat is also small.

Through this, it can be seen that an efficient and selective chemical reaction may be induced only through the Mechanofusion process (Examples 1 to 4).

TABLE 2

| | Peak Temperature (° C.) | Curing calorie (J/g) |
|---|---|---|
| Example 1 | 124.6 | 298.0 |
| Example 2 | 119.7 | 295.5 |
| Example 3 | 119.6 | 297.6 |
| Example 4 | 120.6 | 257.6 |
| Example 5 | 125.6 | 284.7 |
| Example 6 | 120.9 | 270.1 |
| Example 7 | 121.5 | 275.1 |
| Example 8 | 122.2 | 245.0 |
| Example 9 | 123.5 | 302.2 |
| Example 10 | 121.4 | 288.5 |
| Example 11 | 119.8 | 297.5 |
| Example 12 | 120.7 | 255.8 |
| Comparative Example 1 | 119.3 | 301.3 |

Test Example 4—Storage Stability

Figure 6:
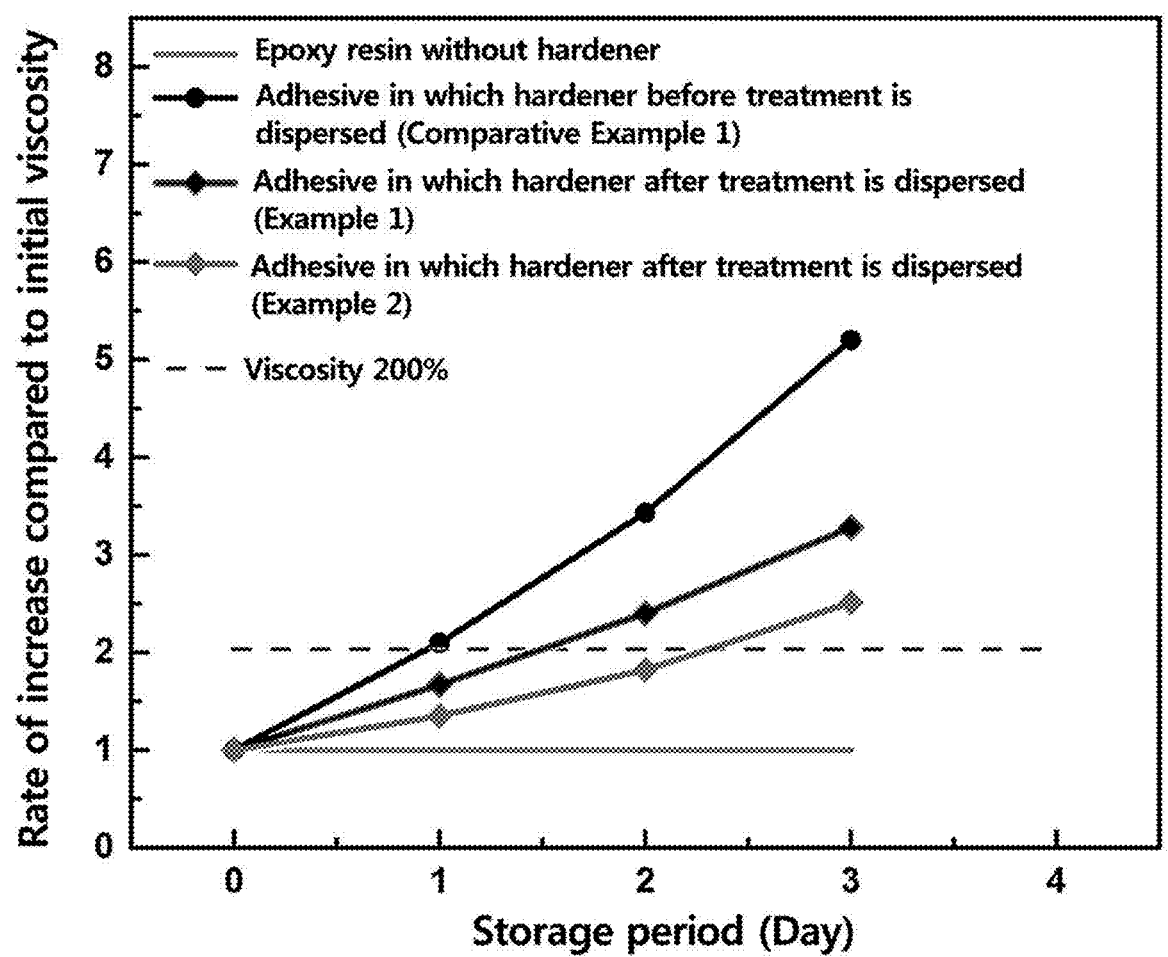
FIG. 6 is a graph illustrating a change in viscosity of a one-component epoxy resin adhesive prepared according to an example of the present disclosure after the adhesive is dispersed in a composite resin in order to test the storage stability of the one-component epoxy adhesive.

After one-component epoxy adhesives (Examples 1 to 12) were prepared by utilizing the surface deactivation-treated latent hardener according to an example of the present disclosure, the one-component epoxy adhesives were stored in an oven at 60° C. for 72 hours, and then the storage stability was observed through a change in viscosity in order to measure the storage stability (Table 3 and FIG. 6).

FIG. 6 is a result of examining the storage stability of the hardener before the surface treatment (Comparative Example 1) and the surface-treated latent hardener (Example 1) in the epoxy resin, and it can be confirmed that the storage stability of the latent hardener is improved.

Referring to the following Table 3, it can be confirmed that when the one-component epoxy adhesive including the latent hardener prepared according to an example of the present disclosure (Example 1) is compared with the one-component epoxy adhesive including a general hardener which is not surface-deactivated (Comparative Example 1), the range of change in viscosity is significantly reduced, and thus, the storage stability is enhanced. Therefore, it can be seen that when a latent hardener composite is prepared according to an embodiment of the present disclosure, the storage stability of the hardener may be enhanced through a simple process.

TABLE 3

| | Initial Viscosity (cPs) | Viscosity (cPs) | Degree (%) of change |
|---|---|---|---|
| Example 1 | 26,000 | 65,500 | 251.92 |
| Example 2 | 25,000 | 82,000 | 328.00 |
| Example 3 | 24,800 | 73,000 | 294.35 |

TABLE 3-continued

|  | Initial Viscosity (cPs) | Viscosity (cPs) | Degree (%) of change |
|---|---|---|---|
| Example 4 | 25,300 | 81,000 | 320.16 |
| Example 5 | 21,500 | 46,400 | 215.81 |
| Example 6 | 23,000 | 65,400 | 284.35 |
| Example 7 | 23,300 | 64,800 | 278.11 |
| Example 8 | 22,000 | 59,000 | 268.18 |
| Example 9 | 27,500 | 72,400 | 263.27 |
| Example 10 | 27,000 | 91,000 | 337.04 |
| Example 11 | 28,000 | 88,800 | 317.14 |
| Example 12 | 27,500 | 78,400 | 285.09 |
| Comparative Example 1 | 27,000 | 100,900 | 373.70 |

In the case of Examples 5 to 8, the curing heat is reduced by approximately 30% as shown in Table 2, so that curing is insufficiently performed even in the result of tracking the viscosity because the reduction in curing heat is a deterioration in function of the hardener. In other words, the viscosity seems to be excellent, but it can be considered that the function as the hardener deteriorates due to the insufficient performance of the curing, or the function deteriorates due to a problem with the reactivity among the curing performances of the hardener.

As described above, according to exemplary embodiments of the present disclosure from the results of Test Examples 1 to 4, the rate of increase in viscosity of the epoxy composite resin over time may be decreased by three times or more, and the pot life may be increased by five times or more. In addition, in the case of a method for treating the surface with different types of nanoparticles, there is a concern in that the viscosity of the hardener may be significantly increased by the unreacted particles, but the method for preparing a latent hardener according to an embodiment of the present disclosure may prevent the side effect of increasing the viscosity due to the residual compound because the residual reactants do not remain. Furthermore, it can be seen that the rate of increase in viscosity of a one-component epoxy adhesive prepared by including the latent hardener was also significantly decreased, and thus, the storage stability was improved.

Further, although the present disclosure has been described in more detail with reference to the illustrated examples, this is only an example, and it is to be understood by a person with ordinary skill in the art to which the present disclosure pertains that various modifications and equivalent other examples may be made.

The method for preparing a latent hardener according to the present disclosure is eco-friendly compared to a wet process because a solvent is not used during the process while increasing the pot life of a one-component epoxy adhesive including a latent hardener which is a product by deactivating the surface of the hardener through a dry high energy-type mixer.

Further, it is possible to selectively deactivate only the surface of a hardener without any chemical modification inside the hardener by injecting carbon dioxide or an inert gas into a dry high energy-type mixer.

In addition, when a process is performed using carbon dioxide, the reaction occurs uniformly as a whole and high reproducibility and homogeneity can be secured because the gas phase is used as a reactant.

Furthermore, since particles or organic materials other than the hardener are not additionally used, it is possible to prevent an increase in viscosity and a change in curing behavior due to the residual unreacted reactants.

While the present disclosure has been described with respect to the specific embodiments, it will be apparent to those skilled in the art that various changes and modifications may be made without departing from the spirit and scope of the invention as defined in the following claims.

What is claimed is:

1. A method for preparing a latent hardener, the method consisting essentially of, in the order recited:
    introducing a hardener into a dry mixer that is a high-energy-type mixer;
    injecting carbon dioxide gas or an inert gas into the dry mixer; and
    mechanochemically deactivating only a surface of the hardener using the dry mixer.

2. The method of claim 1, wherein the hardener is selected from the group consisting of an amine-based adduct, an imidazole-based adduct, dicyandiamide, a dihydride-based compound, a dichlorophenyl dimethylurea compound, and combinations thereof.

3. The method of claim 1, wherein the inert gas is selected from the group consisting of helium, nitrogen, argon, neon, krypton, and combinations thereof.

4. The method of claim 1, wherein the carbon dioxide or inert gas is injected into the dry mixer at a flow rate of 0.1 to 10 L/min, and
    mechanochemically deactivating only the surface of the hardener is performed for a time ranging from 1 to 240 minutes.

5. The method of claim 1, wherein the dry mixer comprises a vessel having an adjustable temperature, a rotating inner vessel, a pressure-applying arm, and a scraper, and
    wherein the method is performed by a condition selected from the group consisting of a rotation speed of the rotating inner vessel, a gap between the rotating inner vessel and the pressure-applying arm, a type of gas, a gas inflow amount, temperature, and combinations thereof.

6. The method of claim 5, wherein the rotation speed of the rotating inner vessel is 20 to 15,000 rpm, the gap between the rotating inner vessel and the pressure-applying arm is 0.2 to 10 mm, and the temperature is 20 to 60° C.

* * * * *